United States Patent [19]

Baldwin et al.

[11] Patent Number: 4,816,457
[45] Date of Patent: Mar. 28, 1989

[54] ARALKYLAMINOETHANOL HETEROCYCLIC COMPOUNDS

[76] Inventors: John J. Baldwin, 621 Gypsy Hill Cir., Gwynedd Valley, Pa. 19446; Joseph Atkinson, 5643 Plantagenet Street, Montreal, Quebec, Canada, H3T 1S3; David E. McClure, 1502 St. Andrews Way, Lansdale, Pa. 19446

[21] Appl. No.: 68,589

[22] Filed: Jun. 30, 1987

Related U.S. Application Data

[60] Continuation-in-part of Ser. No. 783,972, Oct. 3, 1985, Pat. No. 4,686,222, which is a division of Ser. No. 361,673, Mar. 25, 1982, Pat. No. 4,568,679, which is a division of Ser. No. 219,725, Dec. 23, 1980, Pat. No. 4,358,455.

[51] Int. Cl.$^4$ ............... A61K 31/495; A61K 31/505; C07D 239/42; C07D 241/20
[52] U.S. Cl. ............... 514/256; 514/255; 514/275; 544/105; 544/316; 544/336; 544/332; 544/336; 544/377; 544/405; 544/408; 546/117; 546/300; 546/311; 546/312; 546/270; 548/221
[58] Field of Search ............... 544/332, 331, 336, 405; 514/255, 256, 275

[56] References Cited

U.S. PATENT DOCUMENTS 4,171,214 10/1979 Balasubramanyan et al. ..... 544/336
4,560,756 12/1985 Brunnmueller et al. ............ 544/336

*Primary Examiner*—Glennon H. Hollrah
*Assistant Examiner*—James H. Turnipseed
*Attorney, Agent, or Firm*—Edward W. Murray; Michael C. Sudol, Jr.

[57] ABSTRACT

Heterocyclic aminoethanols of the formula:

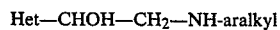

Het—CHOH—CH$_2$—NH-aralkyl where Het is a 6-10 membered N-heterocycle are disclosed. The compounds are useful as pharmaceuticals.

6 Claims, No Drawings

ARALKYLAMINOETHANOL HETEROCYCLIC COMPOUNDS

REFERENCE TO RELATED APPLICATIONS

This is a continuation-in-part of Ser. No. 783,972, filed Oct. 3, 1985, now U.S. Pat. No. 4,686,222, which in term is a division of the copending application Ser. No. 361,673, filed Mar. 25, 1982, now U.S. Pat. No. 4,568,679, which in turn is a division of application Ser. No. 219,725, filed Dec. 23, 1980, now U.S. Pat. No. 4,358,455.

BACKGROUND OF THE INVENTION

The present invention is concerned with heterocyclic compounds of the formula:

Het—CHOH—CH$_2$—NH—aralkyl

Substituted phenylaminoethanols of the formula Ph—CHOH—CH$_2$—NH—aralkyl where Ph is a substituted phenolic group are disclosed in U.S. Pat. Nos. 3,644,353 and 3,705,233. These compounds have random activity as β-adrenergic stimulants and β-adrenergic blockers. These compounds are taught to be useful as pharmaceuticals for treating glaucoma and cardiovascular disorders such as hypertension and arrhythmias.

Heterocyclic aminoethanols which have pharmaceutical utility have been discovered.

SUMMARY OF THE INVENTION

The present invention relates to heterocyclic compounds of the formula Het—CHOH—CH$_2$—NH-aralkyl where Het is 6-10 membered N-heterocyclic and their use as pharmaceuticals.

DESCRIPTION OF THE PREFERRED EMBODIMENTS

An embodiment of the present invention is compounds of the formula:

Het—R

I and pharmaceutically acceptable salts thereof where Het is:

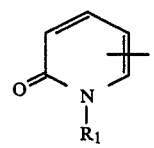

(a)

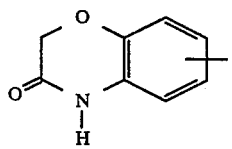

(b)

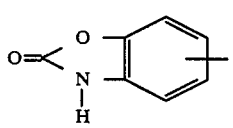

(c)

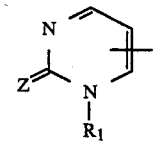

(d)

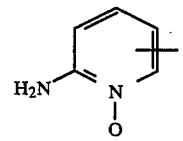

(e)

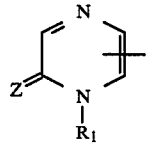

(f)

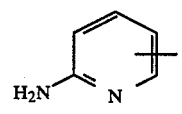

(g)

or

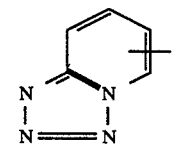

(h)

tautomers thereof, and pharmaceutically acceptable salts thereof wherein:

R$_1$ is H or OH,

Z is O or NH, OH

R is CH—CH$_2$—NHR$_3$ wherein

R$_3$ is

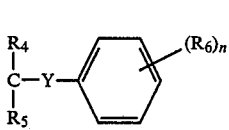

wherein

R$_4$ and R$_5$ are independently selected from H and C$_1$-C$_3$alkyl,

Y is CH$_2$, (CH$_2$)$_2$, (CH$_2$)$_3$, (CH$_2$)$_4$ or —CH$_2$O—

R$_6$ is H, OH, O—C$_1$—C$_3$alkyl, methylenedioxy, halogen or C$_1$-C$_3$alkyl and n is 1 or 2.

The pharmaceutically acceptable salts are the salts of the Formula I base with suitable organic or inorganic acids. Suitable organic acids include carboxylic acids such as acetic acid, pamoic acid, pivalic acid, oxalic acid, lauric acid, pelargonic acid, citric acid, tartaric acid, maleic acid, oleic acid, propanoic acid, succinic acid, isobutyric acid, malic acid and the like, the noncarboxylic acids such as isethionic acid and methane sulfonic acid. Maleic acid salts are preferred. Suitable inorganic acids are the hydrogen halides, e.g. HCl, HI, HBr, phosphoric acid and sulfuric acid. The hydrohalide salts, and especially the hydrochlorides, are preferred. These salts can be prepared by treating the free base with an appropriate amount of a suitable acid, generally in a solvent.

$R_3$ is the phenalkyl group

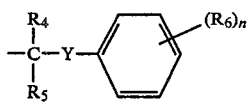

Each of $R_4$ and $R_5$ may be $C_1$-$C_3$alkyl, e.g. $CH_3$, $C_3H_7$, $C_2H_5$ and the like or hydrogen. $CH_3$ and H are preferred $R_4/R_5$ substituents while it is more preferred when one or both of $R_4/R_5$ is $CH_3$. Y is $CH_2O$, $CH_2$ or $(CH_2)_{1-4}$, with $CH_2$ and $(CH_2)_2$ being preferred. $R_6$ is H, OH, O—$C_1$-$C_3$alkyl, halogen (Br, Cl, I or F with Br and Cl being preferred), methylenedioxy or $C_1$-$C_3$-alkyl, branched or linear. H and $OCH_3$ are preferred definitions of $R_6$.

Examples illustrating useful $R_3$ groups are:

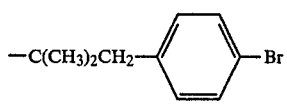

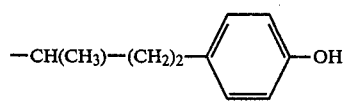

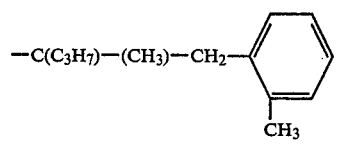

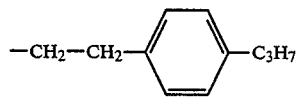

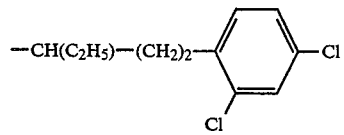

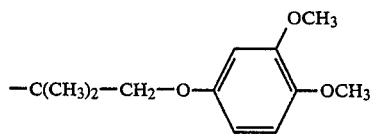

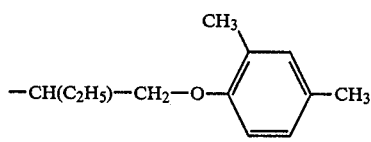

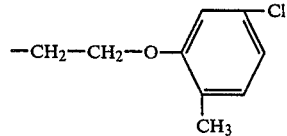

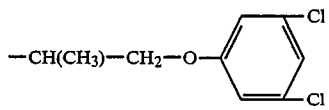

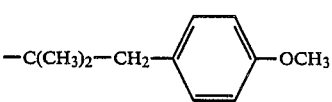

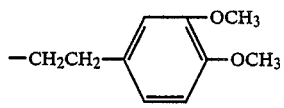

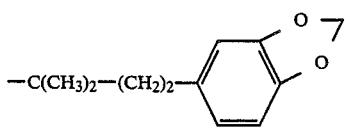

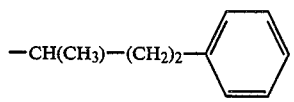

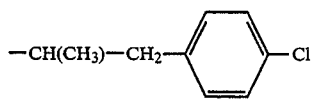

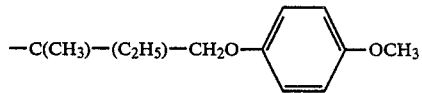

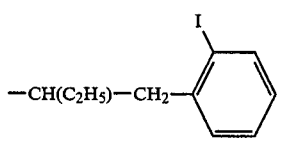

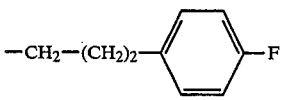

and the like.

Of the heterocyclic groups, the (a), (b), (c), (e), (g) and (h) groups are preferred; the (a), (b), (c), (e) and (g) groups are more preferred; the (a), (b), (e) and (g) groups are especially preferred. The (b), (e) or (g) groups are more particularly preferred.

The monocyclic group:

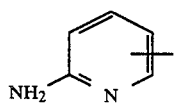

and the bicyclic group:

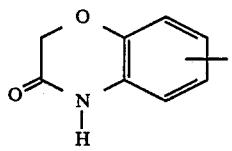

are most preferred. In the heterocyclic groups tautomers occur and are included. An illustrative example of such tautomers is:

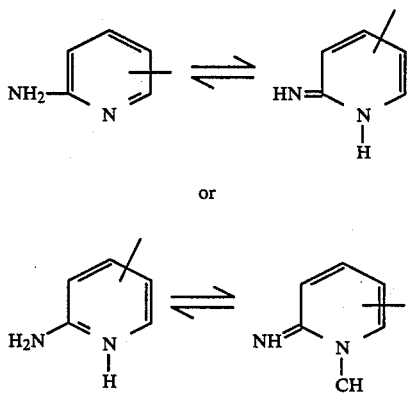

The compounds of formula I have one chiral center at the 1-position in the aminoethanol substituent and can have a second chiral center when the $R_4$ and $R_5$ substituents in the $R_3$ group are different. The chiral centers confer optical activity on the formula I compounds.

All the optical isomer forms, that is mixtures of enantiomers or diastereomers, e.g. racemates as well as individual enantiomers or diasteriomers of formula I, are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stand for sinister and rectus, respectively.

The individual optical isomers may be prepared using conventional resolution procedures, e.g., treatment with an appropriate optically active acid, separating the diasteriomers and then recovering the desired isomer.

A compound of Formula I is useful for treating glaucoma since it decreases intraocular pressure when topically administered to the eye. The ability to lower intraocular pressure is determined using an in-vivo protocol in a rabbit model.

Said compound is preferably administered in the form of an ophthalmic pharmaceutical composition adapted for topical administration to the eye such as a solution, an ointment or as a solid insert. Formulations of the compound may contain from 0.01 to 5% and especially 0.5 to 2% of medicament. Higher dosages as, for example, about 10% or lower dosages can be employed provided the dose is effective in lowering intraocular pressure. As a unit dosage form, between 0.001 to 5.0 mg, preferably 0.005 to 2.0 mg, and especially 0.005 to 1.0 mg of the compound is generally applied to the human eye.

The pharmaceutical composition which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols; vegetable oils; polyalkylene glycols; petroleum based jelly; ethyl cellulose; ethyl oleate; carboxymethylcellulose; polyvinylpyrrolidone; isopropyl myristate, and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes, 1,000, 1,500, 4,000, 6,000 and 10,000 bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetate, glyconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates and as polyacrylic acid salts; natural products such a gelatin, alginates, pectins, tragacanth, karaya, chondrus, agar, acacid; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Del. under the name KLUCEL such as KLUCEL HF, HWF, MF, GF, JF, LF and EF which are intended for food or pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX, a polymer supplied by Union Carbide Co., may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye.

The insert can be of any suitable size to readily fit into the eye. For example, castings or compression molded films having a thickness of about 0.25 mm to 15.0 mm can be subdivided to obtain suitable inserts. Rectangular segments of the cast or compressed film having a thickness between about 0.5 and 1.5 mm can be cut to afford shapes such as rectangular plates of 4×5–20 mm or ovals of comparable size. Similarly, extruded rods having a diameter between about 0.5 and 1.5 mm can be cut into suitable sections to provide the desired amount of polymer. For example, rods of 1.0 to 1.5 mm in diameter and about 20 mm long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the terms smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohols and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer. The insert may contain from about 1 mg to 100 mg of water soluble polymer, more particularly from 5 to 50 mg and especially from 5 to 20 mg. The medicament is present from about 0.1 to about 25% by weight of insert.

The ability of the Formula I compound to lower intraocular pressure is determined in rabbits with experimental glaucoma induced by intraocular injection of α-chymotrypsin. Compounds of Formula I are effective in lowering intraocular pressure after topical application. Pressure is reduced in the normal and the glaucomatous eye.

The compounds (Formula I) of the present invention have β-adrenergic blocking activity. This β-adrenergic blocking activity is determined by measuring the ability of representative compounds to block the β-adrenergic stimulant effect of isoproterenol in a test animal.

The compounds of the present invention also have a α-adrenergic blocking activity. This α-adreneragic blocking activity is determined, (a) in vitro by measuring the ability of a representative Formula I compound to displace radio labeled α-adrenergic antagonist from a tissue substrate or (b) in vivo, by measuring the ability of a representative Formula I compound to block the α-adrenergic stimulant effect of phenylephrine in anesthetized normotensive animals.

The present compounds exhibit antihypertensive activity of immediate onset. This rapid onset antihypertensive activity is determined by administering a representative compound of the present invention to spontaneously hypertensive (SH) rats and measuring the effect on blood pressure.

The α- and β-adrenergic blocking activity of the present compounds indicates that the compounds may be useful in humans for treating cardiovascular conditions susceptible to β-blockade therapy (e.g., angina pectoris, arrhythmia) while minimizing bronchoconstriction via α-adrenergic blockade. This α/β-blocking effect can be useful in treating hypertension caused by pheochromocytoma.

For use as α/β-adrenergic blocking agents, and/or antihypertensive agents the compounds of the present invention can be administered orally, by inhalation, by suppository or parenterally, i.e., intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form required. Conventional procedures are used to prepare the pharmaceutical formulations. The effective daily dosage level for the present compounds for applications other than treatment of the eye may be varied from about 10 mg. to about 3000 mg. Daily doses ranging from about 100 to about 2500 mg. are preferred, with about 200 to about 1000 mg. being a more preferred range. Oral administration is preferred. Either single or multiple daily doses may be administered depending on unit dosage.

Compounds of formula I also have bronchodilator activity. This is determined by measuring the effectiveness of the compound to antagonize slow reacting substance of anaphylaxis (SRS-A). The compounds are thus useful to treat conditions in mammals especially human beings which benefit from bronchodilatation such as asthma, etc. For use as a bronchodilator, the compound is administered orally or parenterally in conventional dosage form such as tablet, capsule, solution, dispersion, emulsion and the like. The compound may also be administered as a spray or an aerosol using an appropriate delivery device and formulation. The oral route is preferred. Sufficient formula I compound is administered to produce the desired level of bronchodilation. Daily dosages for oral or parenteral administration may range from about 1 mg. to about 300 mg., and preferably form about 2 to about 150 mg. Spray or aerosol delivery will be in metered doses ranging from about 50 to about 1000 mcg, administered as needed.

Thus, other embodiments of the present invention are the pharmaceutical compositions containing a therapeutically effective amount of the Formula I compound and methods for (1) treating hypertension, other cardiovascular conditions, or glaucoma, (2) for lowering intraocular pressure, or (3) for effecting bronchodilation.

Compounds of formula I may be prepared by any convenient process. One such useful process is illustrated by the following set of reaction equations:

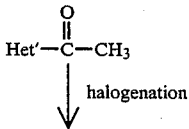

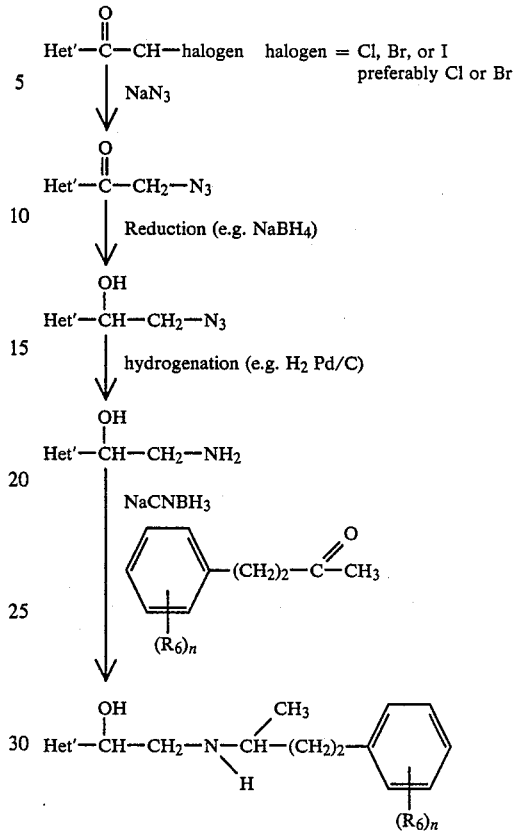

Het' is a heterocyclic group (a), (b), (c) or a suitable precursor thereof.

Another process for preparing some compounds of formula I is illustrated by the following set of reaction equations:

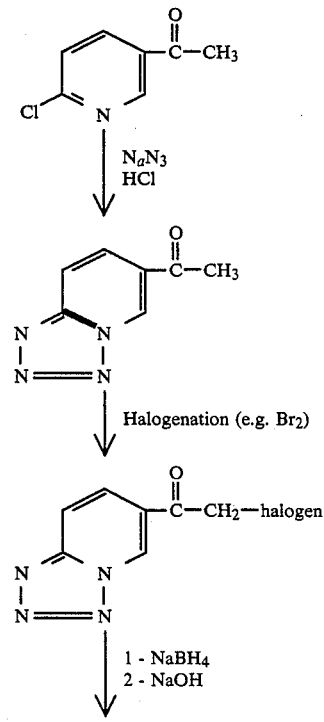

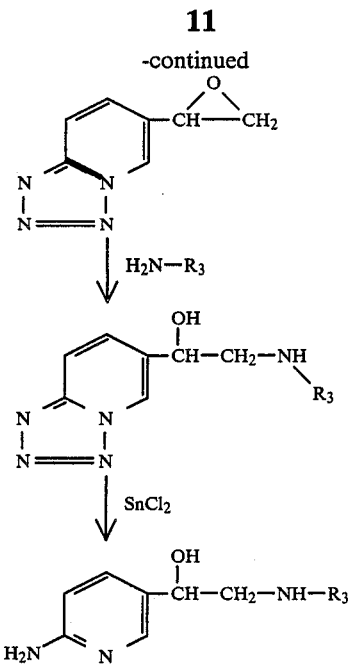
The N-oxide of the formula II compound is prepared as illustrated by the following set of reaction equations:
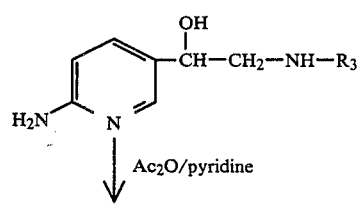
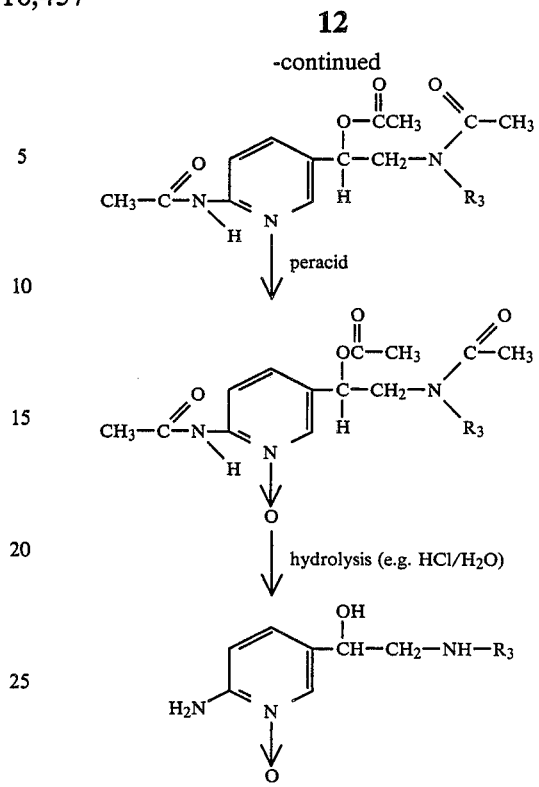
Another process for preparing some compounds of formula I is illustrated by the following set of reaction equations:
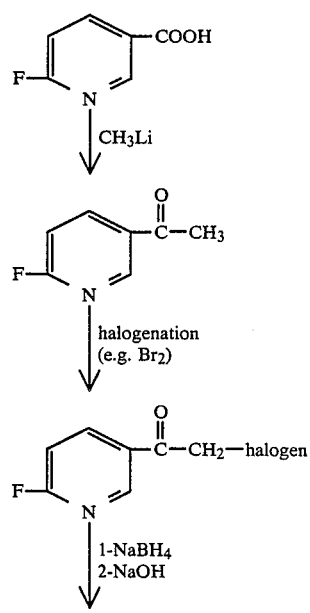

-continued
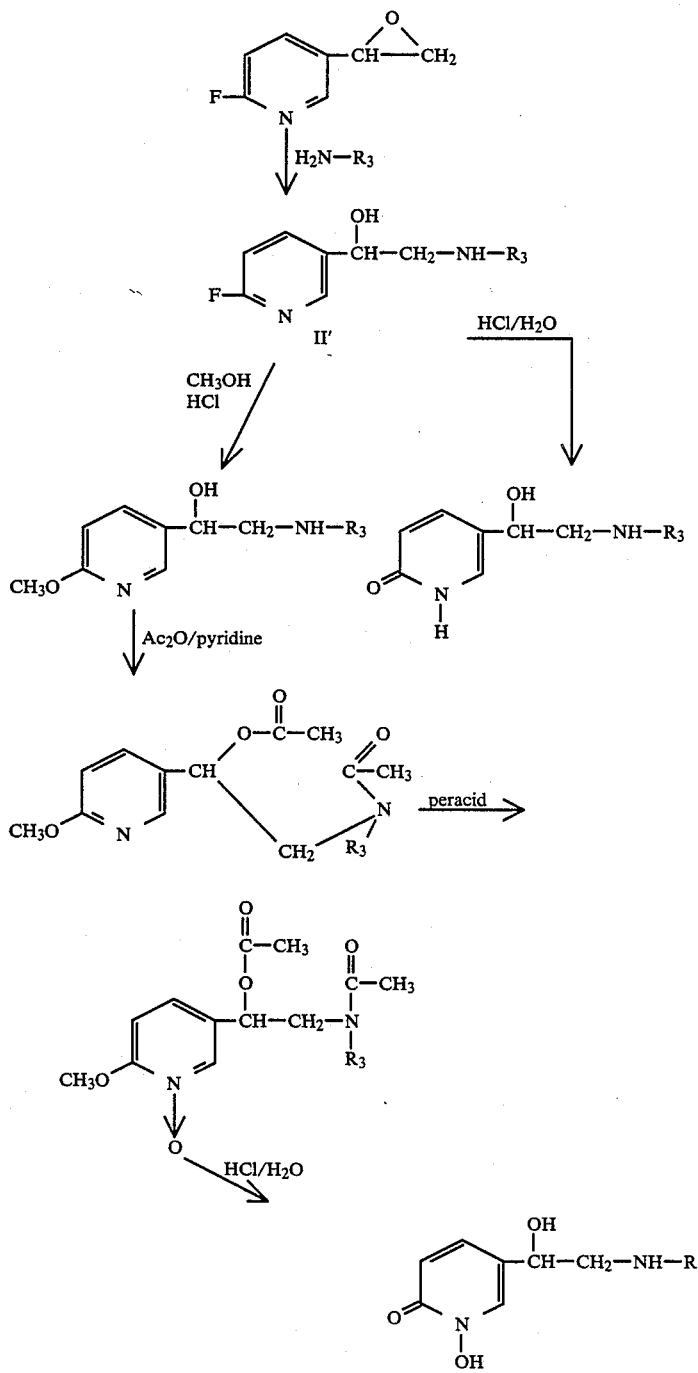
Compounds of the type
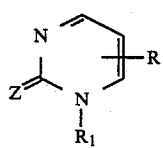
wherein Z is NH which may be represented by the following tautomeric forms
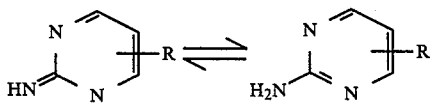
may be prepared by the following sequence of reactions:

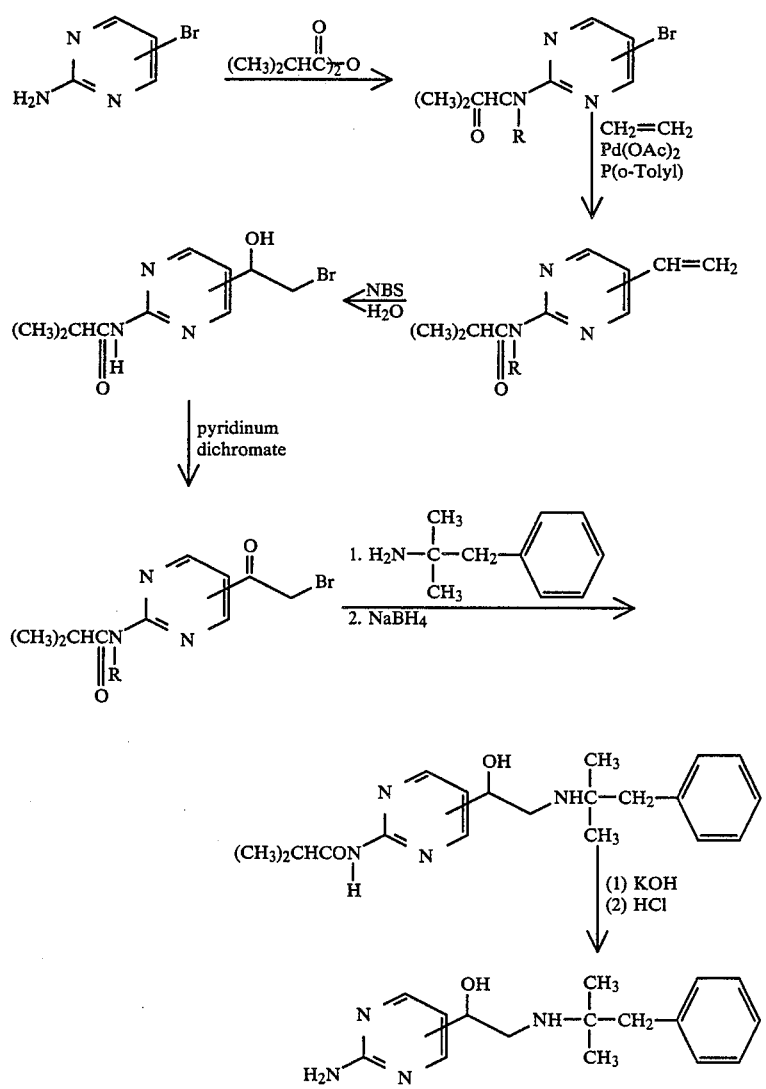

Compounds which may be represented by the tautomeric forms

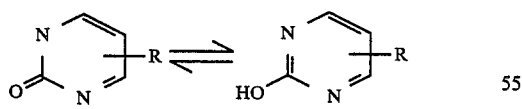

may be prepared from the corresponding 2-amino compound in the following manner.

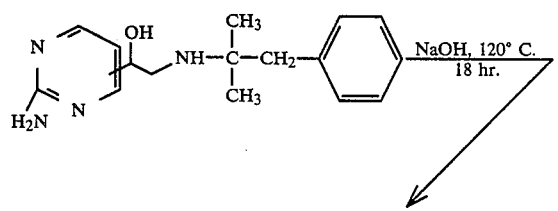

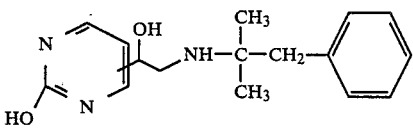

The N-oxides may be prepared as described for the corresponding pyridine compound.

The following examples illustrate preparation of representative compounds of formula I. The processes used are those set out in the sets of equations set out above. All temperatures are in 5 degrees Celsius.

EXAMPLE 1

Preparation of 7-[1-hydroxy-2-(4-phenyl-2-butylamino)-ethyl]-2H-1,4-benzoxazin-3(4H)-one maleate salt of the formula:

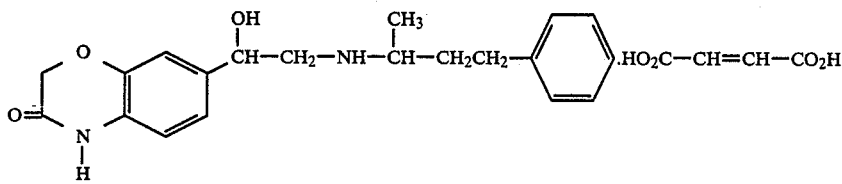

A. 7-Acetyl-2H-1,4-benzoxazin-3(4H)-one (A)

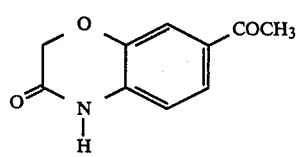

To a stirred mixture of 17.7 gm. (0.117 moles) of 4-amino-3-hydroxyacetophenone (Eur. J. Med. Chem., 9, 491 (1974)) and 35.4 gm. (0.42 moles) of $NaHCO_3$ in a mixture of 350 ml. (0.176 moles) of chloroacetyl chloride over 30 minutes at 25° C. The reaction mixture was then stirred and heated at 90° C. for 5 hours, after which a further 1 ml (0.013 moles) of chloroacetyl chloride was added and heating continued for 2 hours. TLC indicated no starting material remained. The reaction mixture was cooled and poured into 1500 ml of water. After stirring for 1 hour, the precipitate was filtered an air dried to yield 16.3 gm. of A, m.p. 197°–198°. Extraction of the aqueous with ethyl acetate yielded a further 4.5 gm. of A; total yield, 93%.

B. 7-Bromoacetyl-2H-1,4-benzoxazin-3(4H)-one (B)

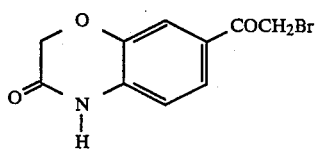

A mixture 4 gm. (20.9 mmoles) of 7-acetyl-2H-1,4-benzoxazin-3(4H)-one and 8.9 gm. (39.9 mmoles) of finely ground cupric bromide in 1000 ml of ethyl acetate was stirred and refluxed for 18 hours. A further 3.6 gm. (16 mmoles) of cupric bromide was added and reflux continued for 6 hours. The reaction mixture was filtered, decolorized with charcoal and upon concentration there was obtained 3.8 gm. (68% yield) of B, m.p. 217°–219° (dec.).

C. 7-Azidoacetyl-2H-1,4-benzoxazin-3(4H)-one (C)

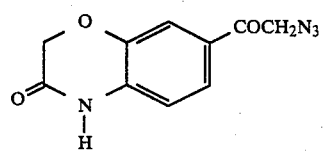

To a suspension of 270 mg. (1 mmole) of 7-bromoacetyl-2H-1,4-benzoxazin-3(4H)-one in 20 ml of methanol was added a solution of 78 mg (1.2 mmoles) of sodium azide in 2 ml of water adjusted to pH 5 with acetic acid. After stirring for 20 hours at 25° C., the precipitate was filtered off, rinsed with water and air dried to give 137 mg (59% yield) of C, m.p. 180° C. (dec.).

D. 7-(1-hydroxy-2-azidoethyl)-2H-1,4-benzoxazin-3(4H)-one (D)

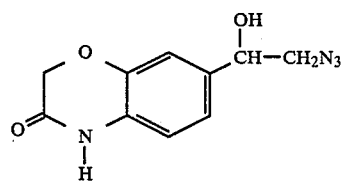

To a solution of 5.6 gm. (24.1 mmoles) of 7-azidoacetyl-2H-1,4-benzoxazin-3(4H)-one in 750 ml of methanol at 50° C. was added 4.56 gm. (120 mmoles) of sodium borohydride was added in portions (vigorous gas evolution). After addition was complete, the reaction was stirred for 1 hour, 50 ml of water and 1.5 ml of acetic added and the mixture evaporated to dryness. Three one hundred millilter portions of methanol were evaporated from the residue, which was then treated with 200 ml of water. After adjusting of the pH to 5 with acetic acid, the aqueous suspension was extracted with 3×200 ml of ethyl acetate. The combined organic extracts were washed with 0.5N acetic acid, 5% $NaHCO_3$, dried ($Na_2SO_4$) and evaporated. Trituration of the residue with 50 ml of ether and filtration gave 4.5 gm. (80% yield of D, m.p. 121°–123° C. (dec.).

E. 7-(1-hydroxy-2-aminoethyl)-2H-1,4-benzoxazin-3(4H)-one hydrochloride

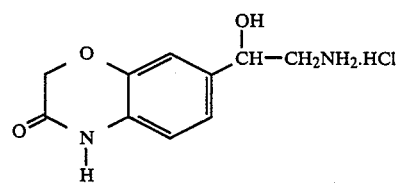

A solution of 4.5 gm. (19.2 mmoles) of D in 120 ml of methanol containing 1 ml of 12N HCl was hydrogenated over 10% Pd/C in a Parr apparatus at 25° C. and 50 p.s.i. for 18 hours. Filtration and evaporation left 4.5 gm. of crude E, which was combined with the crude product from a second hydrogenation of 5.0 gm. of D to give 10.2 gm. of crude E. The free base of E was obtained by passage of an aqueous solution (100 ml) of crude E through 130 ml of AG-50W-X8 cation exchange resin (100–200 mesh) in the acid form, followed by elution with 1.5N $NH_4OH$. Evaporation yielded 5.2 gm. of crude E as the free base, which upon crystallization from 300 ml of ethanol gave 3.62 gm. containing one-fourth of a mole of water: m.p. 179°–182° C.

| Anal. | C | H | N |
|---|---|---|---|
| Calc. | 56.47 | 5.88 | 13.18 |
| Found | 56.26 | 5.83 | 13.17 |

The hydrochloride (E) was prepared in ethanol and after two recrystallization had m.p. 228° C. (dec.).

| Anal. | C | H | N | Cl |
|---|---|---|---|---|
| Calc. | 49.09 | 5.35 | 11.45 | 14.49 |
| Found | 49.19 | 5.63 | 11.32 | 14.31 |

F.
7-[1-hydroxy-2-(4-phenyl-2-butylamine)ethyl]-2H-1,4-benzoxazin-3(4H)-one maleate salt (F)

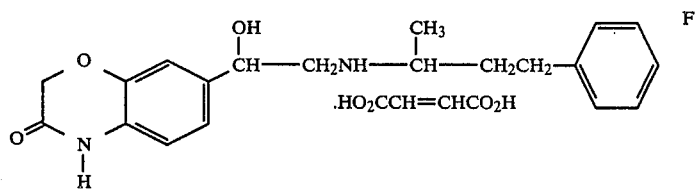

To a solution of 2.3 gm. (11 mmoles) of E free base and 1.5 gm. (6 mmoles) of E in 100 ml of methanol were added 2.5 gm. (17 mmoles) of 4-phenyl-2-butanone and 1.07 gm. (17 mmoles) of sodium cyanoborohydride and the mixture stirred in the presence of 4A molecular sieves at 25° C. for 18 hours. TLC showed no starting materials present and one principal new product. The reaction mixture was acidified with 12N HCl, stirred for 20 minutes, filtered, and evaporated and the residue slurried with ether. The insoluble hygroscopic solid was separated by filtration, suspended in 100 ml of 1N NaHCO3, and the mixture extracted with 3×100 ml of ethyl acetate. The combined organic extracts were washed with water, dried and evaporated to leave 4.2 gm. of solid crude F free base. This was slurried four times with 20 ml of ether to give 2.85 gm. of purified free base. To a hot solution of the free base in ethyl acetate was added a hot solution of 0.97 gm. (8.38 mmoles) of maleic acid in a minimum of ethyl acetate (total volume was 200 ml). Upon seeding and cooling, there was obtained 3.6 gm. of crude F. This was recrystallized from 250 ml of hot acetonitrile by addition of ether to turbidity and cooling to give 2.6 gm. (5.7 mmoles, 34% yield) of F, m.p. 132°–137° C.

| Anal. | C | H | N |
|---|---|---|---|
| Calc. | 63.14 | 6.18 | 6.14 |
| Found | 63.33 | 6.32 | 6.13 |

EXAMPLE 2

Preparation of 6-[1-hydroxy-2-(4-phenyl-2-butylamino)ethyl]-2H-1,4-benzoxazin-3(4H)-one maleate salt of the formula:

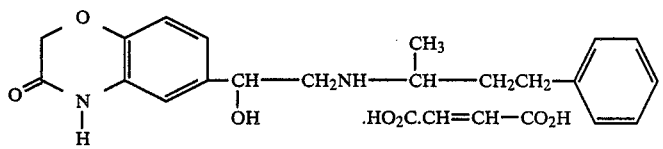

Starting with 6-chloroacety-2H-1,4-benzoxazin-3(4)-one, (C.R. Acad. Sci., C, 270, 1601 (1970), and following essentially the procedures of EXAMPLE I, steps C, D, E and F there were obtained successively:

A. 6-Azidoacetyl-2H-1,4-benzoxazin-3(4H)-one

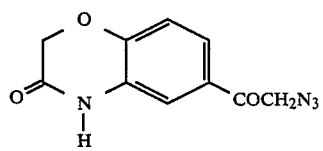

m.p. 177°–178° C. (dec.) 85% yield:

| Anal. | C | H | N |
|---|---|---|---|
| Calc. | 51.72 | 3.47 | 24.13 |
| Found | 51.55 | 3.48 | 23.90 |

B.
6-(1-hydroxy-2-azidoethyl)-2H-1,4-benzoxazin-3-(4H)-one

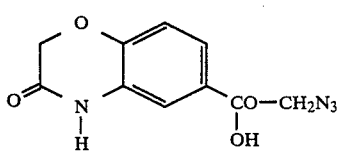

m.p. 137°–138° C., 79% yield

| Anal. | C | H | N |
|---|---|---|---|
| Calc. | 51.28 | 4.30 | 23.92 |
| Found | 51.37 | 4.35 | 24.07 |

C.
6-(1-hydroxy-2-aminoethyl)-2H-1,4-benzoxazin-3-(4H)-one

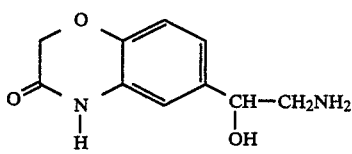

m.p. 175°–178° C., 78% yield

| Anal. | C | H | N |
|---|---|---|---|
| Calc. | 57.68 | 5.81 | 13.46 |
| Found | 57.50 | 5.91 | 13.30 |

D.
6-[1-hydroxy-2-(4-phenyl-2-butylamino)ethyl]-2H-1,4-benzoxazin-3(4H)-one maleate salt

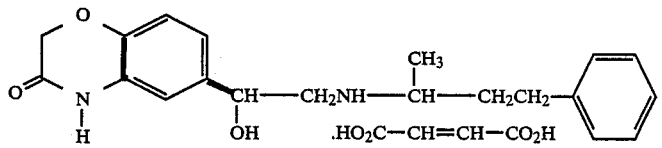

Free base: m.p. 125°–130° C., 83% yield.

| Anal. | C | H | N |
|---|---|---|---|
| Calc. | 70.56 | 7.11 | 8.23 |
| Found | 70.57 | 7.40 | 8.33 |

Maleate: m.p. 154°–157° C., 96% yield

| Anal. | C | H | N |
|---|---|---|---|
| Calc. | 63.14 | 6.18 | 6.14 |
| Found | 63.25 | 6.19 | 6.20 |

EXAMPLE 3

Preparation of 2,3-dihydro-α-{[(1-methyl-3-phenylpropyl)amino]methyl}-2-oxo-6-benzoxazolemethanol maleate salt of the formula

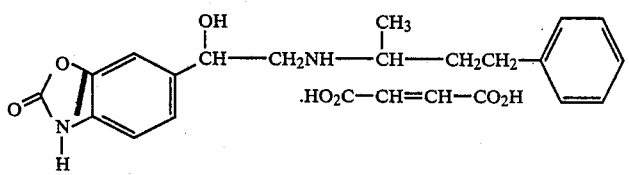

Starting with 6-chloroacetyl-2,3-dihydro-2-oxo-benzoxazole (Eur. J. Med. Chem., 9, 491 (1974), and following essentially the procedures of Example 1, steps C, D, E and F, there were obtained successively:

A. 6-Azidoacetyl-2,3-dihydro-2-oxobenzoxazole

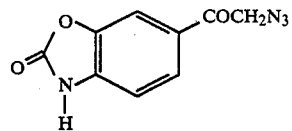

m.p. 250° C. (dec.), 78% yield.

| Anal. | C | H | N |
|---|---|---|---|
| Calc. | 49.55 | 2.77 | 25.68 |
| Found | 49.71 | 2.90 | 24.14 |

B.
2,3-Dihydro-α-(azidomethyl)-2-oxo-6-benzoxazolemethanol

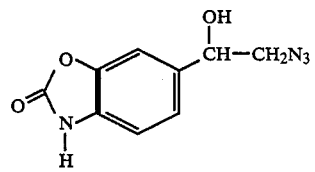

m.p. 119°–121.5° C., 78% yield

| Anal. | C | H | N |
|---|---|---|---|
| Calc. | 49.09 | 3.66 | 25.44 |
| Found | 49.01 | 3.76 | 23.47 |

C.
2,3-Dihydro-α-(aminomethyl)-2-oxo-6-benzoxazolemethanol HCl

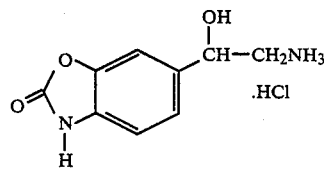

m.p. 315° C., (dec.) 60% yield

| Anal. | C | H | N | Cl |
|---|---|---|---|---|
| Calc. | 46.86 | 4.81 | 12.14 | 15.37 |
| Found | 47.10 | 4.89 | 11.75 | 15.15 |

D. 2,3-Dihydro-α{[(1-methyl-3-phenylpropyl)amino]methyl}-2-oxo-6-benzoxazolemethanol maleate salt

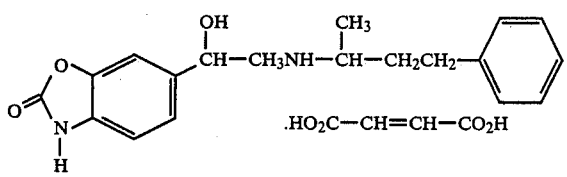

m.p. 163°–165° C., 31% yield

| Anal. | C | H | N |
|---|---|---|---|
| Calc. | 62.43 | 5.92 | 6.33 |
| Found | 62.75 | 6.03 | 6.34 |

EXAMPLE 4

Preparation of 6-amino-α{[(1-methyl-3-phenylpropyl)amino]methyl]}-3-pyridinemethanol dihydrochloride salt of formula:

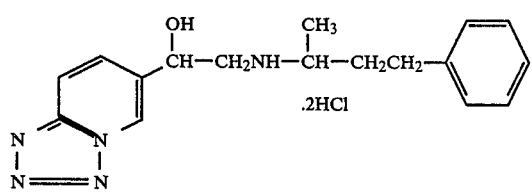

A. 6-Acetyl tetrazolo[1,5-a] pyridine (A)

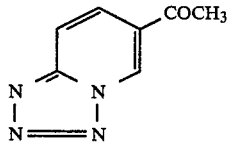

To a stirred solution of 8.4 gm. (51.6 mmoles) of 2-chloro-5-acetylpyridine and 8.4 gm. (129 mmoles) of sodium azide in 150 ml of ethanol and 150 ml of water was added 75 ml of 10% HCl over a period of 20 minutes. The reaction mixture was then heated to reflux for 18 hours, cooled in an ice bath and the resulting crystals filtered off to give a first crop of 6.0 gm. A second crop of 1.0 gm. was obtained for a total of 7.0 gm. of A, (84.% yield), m.p. 159°–160° C.

| Anal. | C | H | N |
|---|---|---|---|
| Calc. | 51.85 | 3.73 | 34.56 |
| Found | 52.01 | 3.91 | 34.40 |

B. 6-Bromoacetyltetrazolo[1,5-a] pyridine (B)

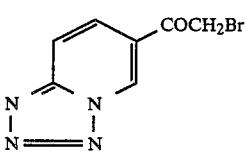

To a partial solution of 55.4 gm. (0.34 moles) of A in 1500 ml of glacial acetic acid, saturated with HBr, and cooled in an ice bath was added a solution of 57 gm. (0.32 moles) of bromine in 500 ml of glacial acetic acid over a period of 2 hours. The reaction was evaporated to dryness and the residue taken up in ethyl acetate. A small amount of insoluble material was filtered off and the ethyl acetate was washed with water, 1N NaHCO₃ solution and dried (Na₂SO₄). Evaporation left 82.4 gm. of crude product which contained 80% of B. A portion (71 gm.) of the crude material was slurried twice with 500 ml of 10% ethyl acetate in ether to give 56 gm. of B, sufficiently pure for further use (79% yield). A sample recrystallized from ethanol had m.p. 110°–113° C.

| Anal. | C | H | N | Br |
|---|---|---|---|---|
| Calc. | 34.88 | 2.09 | 23.24 | 33.15 |
| Found | 35.05 | 2.12 | 23.14 | 33.36 |

C. 2-(tetrazolo[1,5-a] pyrid-6-yl)oxirane (C)

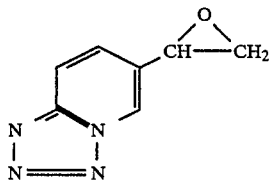

To a suspension of 37 gm. (154 mmoles) of B in 280 ml of methanol was added 1.85 gm. (49 mmoles) of sodium borohydride with stirring at 20° C. over a period of 30 minutes. The reaction mixture was evaporated to dryness and agitated well with a mixture of 500 ml of ethyl acetate and 500 ml of 1N NaOH. The organic layer was separated, washed with water, decolorized with charcoal, dried and evaporated to leave an oily solid. This was chromatographed over silica gel using ethyl acetate.

The partially purified material thus obtained was crystallized from 130 ml of ethanol to give 18.2 gm. (73% yield), of C, m.p. 108°–110° C.

| Anal. | C | H | N |
|---|---|---|---|
| Calc. | 51.85 | 3.73 | 34.56 |
| Found | 51.71 | 3.53 | 34.34 |

D.
α-[(1-methyl-3-phenylpropyl)amino]methyl-6-tetrazolo[1,5-a]pyridinemethanol (D)

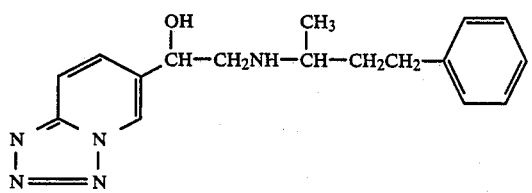

A solution 10 gm. (61.7 mmoles) of C and 10 gm. (67.1 mmoles) of 4-phenyl-2-aminobutane in 50 ml of ethanol was heated to reflux for 1.5 hours. The reaction mixture was evaporated and the residue crystallized first from a minimum of ethyl acetate and recrystallized from 100 ml of ethanol to give 11.4 gm. of D. A second crop 2.3 gm. obtained by chromatography of the mother liquors to give a total of 13.7 gm. (71% yield) of D, m.p. 117°–120° C.

| Anal. | C | H | N |
|---|---|---|---|
| Calc. | 65.57 | 6.80 | 22.48 |
| Found | 65.57 | 6.95 | 22.48 |

The maleate salt was prepared in ethylacetate: m.p. 121°–124° C.

| Anal. | C | H | N |
|---|---|---|---|
| Calc. | 59.00 | 5.90 | 16.39 |
| Found | 59.29 | 6.13 | 16.31 |

E.
6-Amino-α[(1-methyl-3-phenylpropyl)amino]methyl-3-pyridinemethanol dihydrochloride (E)

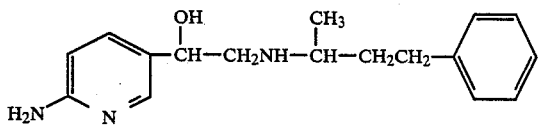

A solution of 11 gm. (35.4 mmoles) of D and 24 gm. (106 mmoles) of stannous chloride dihydrate in 60 ml of 12N HCl is heated to reflux for 2 hours. The reaction was evaporated to dryness, the residue suspended in 150 ml of methanol and basified with concentrated NH₄OH. The precipitated salts were removed by filtration and the product in the filtrate chromatographed over 600 gm. of silica gel, eluting with a mixture of CH₂Cl₂:CH₃OH:concentrated NH₄OH (15:5:4), to give, upon evaporation of the eluate, 6.8 gm. (67% yield) of the free base of E.

The dihydrochloride salt was prepared from the free base in ethanol, by addition of 12N HCl and cooling, in 65% yield. m.p. 156°–158° C.

| Anal. | C | H | N | Br |
|---|---|---|---|---|
| Calc. | 56.98 | 7.03 | 11.73 | 19.79 |
| Found | 56.58 | 7.32 | 11.29 | 19.96 |

The product E is a racemic mixture of diastereomers containing the 4 isomers S,S; S,R; R,S and R,R. By using a specific isomer of the amine reactant in step D., for example, S-4-phenyl-2-aminobutane, a mixture of 2 isomers of E i.e. S,S-E free base and R,S-E free base, is obtained. This mixture is conventionally separated, for example, by chromatography, and the individual isomers i.e. S,S-E free base and R,S-E free base, are obtained. When R-4-phenyl-2-aminobutane is used, the corresponding S,R and R,R isomers of E free base are obtained. This procedure for preparing individual isomers may be used for the preparation of any Formula I compound which involves the reaction of an epoxide and an amine.

EXAMPLE 5
Preparation of 6-amino-α-{[(1,1-dimethyl-3-phenylpropyl)amino]methyl}-3-pyridinemethanol dihydrochloride hemihydrate:

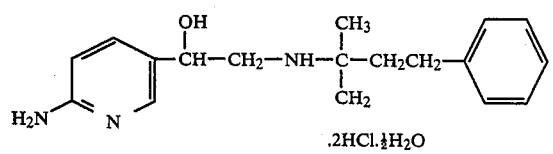

Starting with 4-phenyl-2-amino-2-methylbutane and the product C of Example IV, and following essentially the procedure of Example IV, steps D and E, there was obtained successively:

A.
α-{[1,1-dimethyl-3-phenylpropyl)amino]methyl}-6-tetrazolo[1,5-a]-pyridinemethanol (A)

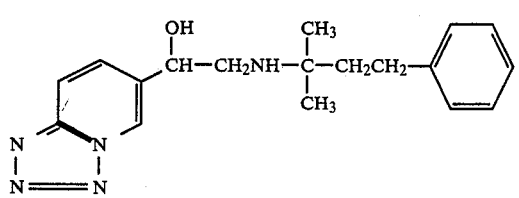

m.p. 126°–127° C. 76% yield.

| Anal. | C | H | N |
|---|---|---|---|
| Calc. | 66.44 | 7.12 | 21.52 |
| Found | 66.70 | 7.20 | 21.37 |

The maleate salt was prepared in ethylacetate: m.p. 167°–168° C., 98% yield.

| Anal. | C | H | N |
|---|---|---|---|
| Calc. | 59.85 | 6.16 | 15.86 |
| Found | 59.88 | 6.35 | 15.74 |

B.
6-Amino-α-}[(1,1-dimethyl(-3-phenylpropyl)amino]methyl}-3-pyridinemethanol dihydrochloride hemihydrate

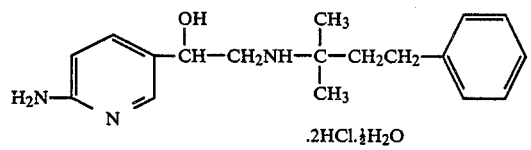

.2HCl.½H₂O m.p. 185°–188° C. (dec.)., 54% yield

| Anal. | C | H | N | Cl |
|---|---|---|---|---|
| Calc. | 56.69 | 7.14 | 11.02 | 18.60 |
| Found | 56.96 | 7.18 | 11.04 | 18.54 |

EXAMPLE 6

Preparation of 6-amino-α-{[1-methyl-3-phenylpropyl)amino]methyl}-3-pyridinemethanol-1-oxide dihydrochloride salt A

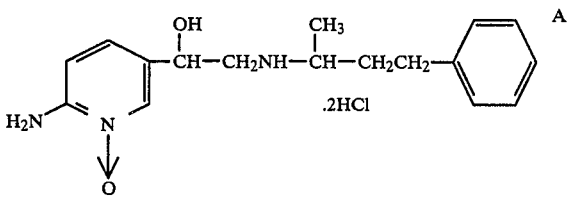

A solution of 2.0 gm. (7.02 mmoles) of the free base of the product of step E of Example 4 in a mixture of 20 ml of pyridine and 10 ml of acetic anhydride was stirred at 20° C. for 18 hours. The excess reactants were evaporated and the residue partitioned between 150 ml of water and 150 ml of ethyl acetate. The organic layer was washed with 1N Na₂CO₃ solution, dried and evaporated to give 2.6 gm. (90% yield) of the triacetylated intermediate.

The protected intermediate was dissolved in 30 ml of chloroform and 1.4 gm. (25% excess) of m-chloroperbenzoic acid was added. After stirring the solution for 3 hours at 20° C., 2 gm. of Ca(OH)₂ powder was added and stirring continued for 30 minutes. The reaction was filtered, the filtrate evaporated and the residue (2.3 gm.) was chromatographed over 400 gm. of silica gel eluting with 10% methanol in ethyl acetate. Two fractions were obtained: (a) 0.50 gm., a single diastereoisomer (b) 1.71 gm. a 1:1 mixture of diastereoisomers (2.21 gm., 82% yield).

The material from fraction (b) was dissolved in 25 ml of 6N HCl and heated to reflux for 3 hours, and the reaction mixture then evaporated to dryness.

The residue was dissolved in methanol, basified with concentrated NH₄OH, and reevaporated to dryness. The residue, containing the free base, was chromatographed over 100 gm. of silica gel using methanol-methylene chloride-concentrated NH₄OH (20:80:3) as eluant. The fractions containing the desired product were combined and treated with HCl in 10 ml. of ethanol. Evaporation and trituration of the residue with ether gave 1.0 gm. (67% yield) of A. m.p. 203°–210° C. (dec), 49% overall yield.

| Anal. | C | H | N | Cl |
|---|---|---|---|---|
| Calc. | 54.56 | 6.73 | 11.23 | 18.95 |
| Found | 54.46 | 6.93 | 11.10 | 18.95 |

EXAMPLE 7

Preparation of 5-{1-hydroxy-2-[(1-methyl-3-phenylpropyl)-amino]ethyl}-2(1H)-pyridinone fumarate hydrate ![structure](...)

.OH₂C—CH=CH—CO₂H.H₂O

A. 5-Acetyl-2-fluoropyridine (A)

![structure A: F-pyridine-COCH₃]

To a suspension of 20 gm. (142 mmoles) of 2-fluoro-5-pyridinecarboxylic acid (J. Am. Chem. Soc., 71, 1125 (1949)) in 750 ml of ether, stirred and cooled in ice, was added 225 ml of 1.6M methyl lithium (360 mmoles) in ether over 1 hour. The reaction was stirred for an additional 2 hours, then 300 ml of ice water was added. The aqueous layer was washed with 2×100 ml fresh ether, acidified and extracted with ether to give 5.0 gm. (25%) of unreacted starting acid.

The original ether solution was rinsed with water, dried and evaporated to yield 12.2 gm. of crude crystalline A, containing about 15% of the corresponding t-alcohol. Chromatography over silica gel, eluting with 5% ethyl acetate in methylene chloride gave 7.81 gm. (52% yield) of A. A sample crystallized from hexane had m.p. 43°–44° C.

| Anal. | C | H | N | F |
|---|---|---|---|---|
| Calc. | 60.43 | 4.35 | 10.07 | 13.65 |
| Found | 60.17 | 4.33 | 9.97 | 12.96 |

B. 5-Bromoacetyl-2-fluoropyridine (B)

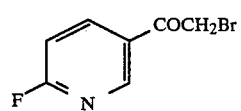

Starting with 14 gm. (100 mmoles) of A, and following the procedure described in Example 4, Step B, there was obtained 18.6 gm. of crude B, which consists of 7% of A, 82% of B and 11% of dibromoketone. This material was used without further purification for the next step.

C. (2-fluoropyrid-5-yl)oxirance (C)

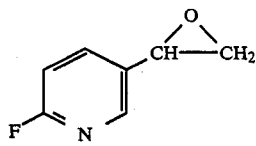

Starting with 18.6 gm. of crude B and following essentially the procedure of Example 4, Step C, there was obtained 13.4 gm. of crude C, which was suitable for use in the next step without further purification.

D. 6-Fluoro-α-{[1-methyl-3-phenylpropyl)amino]-methyl}-3-pyridinemethanol (D)

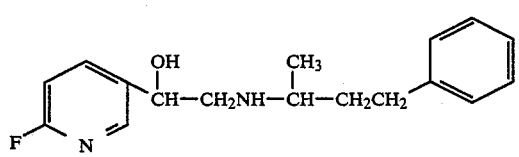

Starting with 15 gm. of crude C (containing ca. 67% of epoxide) and following essentially the procedure described in Example 4, Step D, there was obtained after chromatography, 10.04 gm. (48% yield) of D, m.p. 81°–86° C.

| Anal. | C | H | N | F |
|---|---|---|---|---|
| Calc. | 70.81 | 7.34 | 9.71 | 6.59 |
| Found | 70.61 | 7.45 | 9.69 | 6.43 |

E. 5-{1-hydroxy-2[(1-methyl-3-phenylpropyl)amino]-ethyl}-2(1H)-pyridinone fumarate hydrate (E)

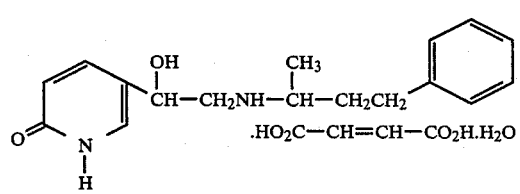

A solution of 2.03 gm. (7.0 mmoles) of D in 25 ml of 2N HCl was heated to reflux for 6 hours. The reaction mixture was evaporated to dryness, re-dissolved in water and basified with $NaHCO_3$. The resulting mixture was evaporated to dryness, the residue exhaustively extracted with hot ethyl acetate and, after drying, the ethyl acetate was evaporated to yield 1.9 gm. of an oil (the free base of E). A sample crystallized to give m.p. 85°–89° C.

The salt was prepared by adding a solution of fumaric acid (1.4 gm) in methanol (15 ml) to the base (3.15 gm) dissolved in equal quantities of acetonitrile and methanol (250 ml total), and evaporating the solution to about 50 ml volume. After 2 hours there was obtained, upon filtration of the resulting crystals, 3.7 gm (75% yield) of E, m.p. 185°–189° C. (dec.)

| Anal. | C | H | N |
|---|---|---|---|
| Calc. | 59.99 | 6.71 | 6.66 |
| Found | 59.49 | 6.33 | 6.41 |

EXAMPLE 8

Preparation of 5-{1-hydroxy-2-[(1,1-dimethyl-3-phenylpropyl)-amino]ethyl}-2(1H)-pyridinone dihydrochloride

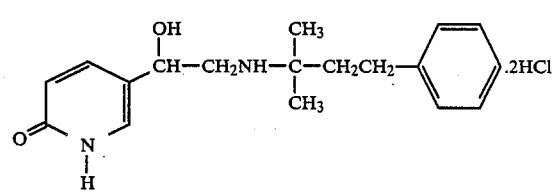

Starting with the epoxide C of Example 7, and reacting it with 4-phenyl-2-amino-2-methylbutane, and proceeding essentially according to Example 7, Steps D and E, there was obtained successively:

A. 6-Fluoro-α-{[(1,1-dimethyl-3-phenylpropyl)amino]-methyl}-3-pyridinemethanol (A)

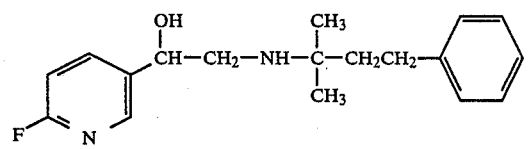

m.p. 116°–118° C., 48% yield.

| Anal. | C | H | N | F |
|---|---|---|---|---|
| Calc. | 71.50 | 7.66 | 9.26 | 6.28 |
| Found | 71.46 | 7.74 | 9.08 | 6.04 |

B. 5-{1-hydroxy-2[(1,1-dimethyl-3-phenylpropyl)-amino]-ethyl}-2(1H)-pyridinone dihydrochloride

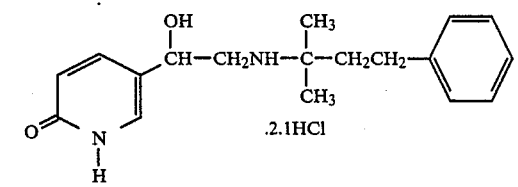

m.p. 179°–181° C., 65% yield.

| Anal. | C | H | N | F |
|---|---|---|---|---|
| Calc. | 57.35 | 6.97 | 7.43 | 19.74 |
| Found | 56.91 | 6.94 | 7.73 | 19.93 |

EXAMPLE 9

Preparation of
1-hydroxy-5-{(1-hydroxy-2-[(1-methyl-3-phenylpropyl)amino]ethyl}-2(1H)-pyridinone hydrochloride

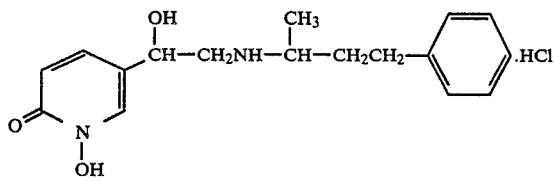

A.
6-Methoxy-α-{[(1-methyl-3-phenylpropyl)amino]methyl}-3-pyridinemethanol (A)

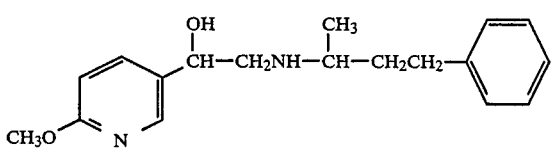

To a solution of 5.9 gm. (20.5 mmoles) of product D from Example 7 in 200 ml methanol was added 2 ml of 12N HCl, and the reaction stirred at 20° C. It was analyzed periodically by NMR and tlc, and additional quantities of 12N HCl were added as follows until the reaction was complete: 6 days—2 ml, 11 days, 2 ml, 17 days—reaction complete. The mixture was evaporated to dryness, partitioned between 1N NaHCO3 and ethyl acetate, and the organic layer evaporated to give 4.8 gm (79% yield) of A, m.p. 80°-83° C., containing a small amount of the corresponding pyridone.

B.
6-Methoxy-α-{[(1-methyl-3-phenylpropyl)amino]methyl}-3-pyridinemethanol-1-oxide-O,N-diacetyl derivative (B)

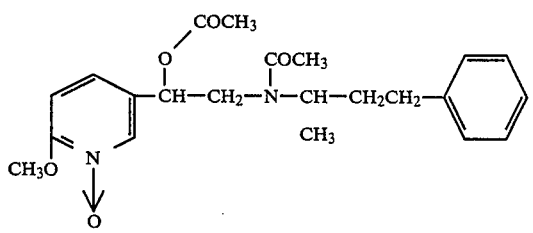

A solution of 4.6 (15.3 mmoles) of A in 250 ml of pyridine and 20 ml of acetic anhydride was stirred at 20° C. for 18 hours. The reaction mixture was then evaporated to dryness and the residue taken up in ethyl acetate, washed with 1N NaHCO3 and water, and evaporated. The residual oil (6.6 gm) was dissolved in 500 ml of chloroform and 6 gm (34 mmoles) of meta-chloroperbenzoic acid was added with stirring at 20° C. After 4 days the reaction was complete and 5.3 gm of Ca(OH)2 was added to the mixture. After 30 minutes, the reaction was filtered and evaporated to leave 8 gm of an oil, which was chromatographed over silica gel using 10% methanol in methylene chloride as elutant. There was recovered about 2.7 gm (45%) of the unoxidized O,N-diacetyl derivative followed by 0.4 gm (6.5%) of a single isomer of B, m.p. 139°-140° C.

| Anal. | C | H | N |
|---|---|---|---|
| Calc. | 65.98 | 7.05 | 6.99 |
| Found | 66.00 | 7.18 | 7.03 |

Continued elution gave 2.1 gm (34% yield) of B as an oily mixture of diastereoisomers, used as such for the subsequent step.

C.
1-Hydroxy-5-{1-hydroxy-2-[(1-methyl-3-phenylpropyl)-amino]ethyl}-2(1H)-pyridinone hydrochloride (C)

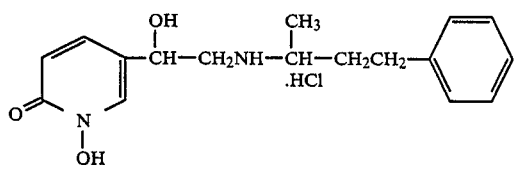

A solution of 2.6 gm (6.5 mmoles) of B in 100 ml of 2N HCl was heated to reflux for 20 hours; analysis by NMR showed hydrolysis and cleavage to be complete. The solution was treated with charcoal, extracted with ether, and evaporated to dryness to give a very hygroscopic solid. It was dissolved in methanol-water and neutralized with concentrated NH4OH. The solution of free base was absorbed onto an ion exchange column (AG5OW-X8, 100–200 mesh, H+ form), and then eluted with 5% NH4OH. Evaporation of the eluate 1.8 gm of crude C as the free base.

Evaporation of 1.5 gm of C free base and 0.265 gm of NH4Cl dissolved in 50 ml of methanol yielded the hydrochloride salt. THe residue was slurried in 25 ml of acetonitrile for 3 days, filtered and air dried to give 1.3 gm (58% yield) of C, m.p. 188° C. (dec.).

EXAMPLE 10

Preparation of
2-Amino-α-{[(1,1-dimethyl-2-phenylethyl)amino]methyl}-5-pyridinemethanol hydrochloride

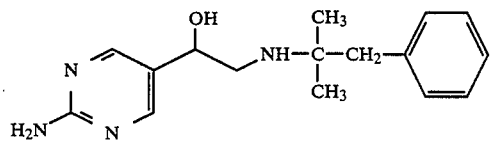

A. 5-Bromo-2-(isobutyramido)pyrimidine

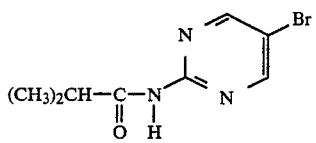

A suspension of 20 g. of 2-amino-5-bromopyrimidine (Chem. Abstr., 54, 11037 (1960)) and 14.78 g. of 4-dimethylaminopyridine in 200 ml of pyridine was stirred with 80 ml of isobutyric anhydride. THe reaction mixture was cooled and then diluted with 1500 ml of water.

The mixture was thoroughly mixed for 30 minutes and then extracted with ether (3×300 ml). The ether extracts were washed with saturated sodium chloride solution (3×300 ml) and then dried over anhydrous magnesium sulfate. Concentration of the organic solution resulted 22.39 g. of crude product which upon recrystallization from benzene (50 ml) yielded 14.5 g. of pure 5-bromo-2-(isobutyramido)-pyrimidine, m.p. 145°–148° C.

B. 5-Ethenyl-2-(isobutyramido)pyrimidine

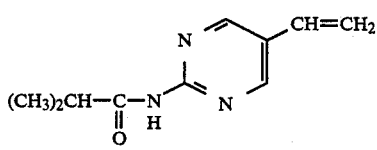

A glass-lined pressure vessel was charged with 4.85 g. of 5-bromo-2-(isobutyramido)pyrimidine, 5.0 ml of triethylamine, 15 ml of acetonitrile, 245 mg. of tris(o-tolyl)phosphine, and 55 mg. of palladium acetate. The vessel was placed under an ethylene atmosphere at 200 psi and heated at 80° C. for 18 hours in a rocking autoclave. The vessel was cooled and then vented. The residue was treated with 50 ml of ether and the resulting mixture filtered. The solid was further washed with ether (2×25 ml). The organic filtrate was concentrated and then chromatographed on silica gel. Elution with ethylene chloride:methanol (95:5) yielded 2.99 g. of 5-ethenyl-2-isobutyramido)pyrimidine, m.p. 110°–112° C.

C. 2-Isobutyramido-5-(1-hydroxy-2-bromoethyl)-pyrimidine

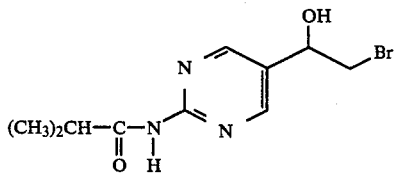

To a solution of 764 mg. of 5-ethenyl-2-(isobutyramido)-pyrimidine in a mixture of 3 ml of water and 7 ml. of tetrahydrofuran, 710 mg. of N-bromosuccinimide was added. The reaction mixture was stirred at room temperature for 18 hours and then partially concentrated under reduced pressure. To the aqueous residue 25 ml of methylene chloride was added and the layers separated. The aqueous layer was further extracted with methylene chloride (20 ml). The combined organic extracts were washed with 20 ml of water and then dried over anhydrous magnesium sulfate. Concentration yielded 977 mg of a glassy product. This material was chromatographed on silica gel (95:5 methylene chloride:methanol) to obtain 491 mg of purified 2-isobutyramido-5-(1-hydroxy-2-bromoethyl)pyrimidine.

D. 2-Isobutyramido-5-(bromoacetyl)pyrimidine

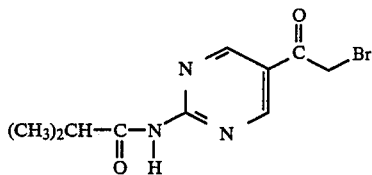

To a solution of 450 mg of 2-isobutyramido-5-(1-hydroxyl-2-bromoethyl)pyrimidine and 120 mg. of pyridinium trifluoroacetate in 20 ml of methylene chloride, 880 mg of pyridinium dichromate is added. The resulting mixture is stirred for 3 hours at room temperature after which the reaction mixture is chromatographed quickly to obtain the desired 2-isobutyramido-5-(bromoacetyl)pyrimidine product.

E. 2-Isobutyramido-α-{[(1,1-dimethyl-2-phenylethyl)amino]methyl}-5-pyrimidinemethanol

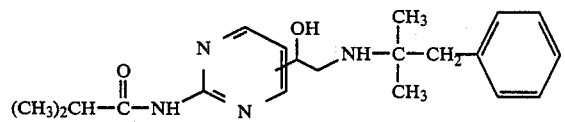

A solution of 342 mg. of 2-isobutyramido-5-(bromoacetyl)pyrimidine in 10 ml of dry tetrahydrofuran is added slowly to a stirred solution of 179 mg of 1,1-dimethylphenethylamine and 136 mg of triethylamine in 2 ml of tetrahydrofuran. The mixture is stirred for 12 hours at room temperature before the removal of the precipitated triethylamine hydrobromide by filtration. The filtrate is concentrated under reduced pressure and the residue redissolved in 15 ml of methanol. To this methanolic solution, 200 mg of sodium borohydride is added and the mixture is stirred for 3 hours at room temperature. The reaction mixture is then added to 50 ml of water and acidified with acetic acid. The mixture is basified with sodium bicarbonate and extracted with dichloromethane (3×50 ml). The combined organic solutions are backwashed with water and then dried over anhydrous magnesium sulfate. Concentration of this solution results in a crude product. Chromatography on silica gel yields a pure product.

F. 2-Amino-α-{[(1,1-dimethyl-2-phenylethyl)amino]methyl}-5-pyrimidinemethanol hydrochloride

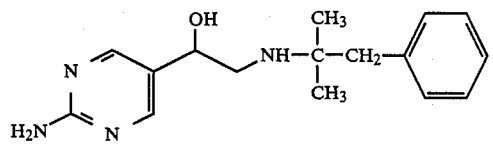

To a solution of 250 mg of 2-isobutyramido-α-{[(1,1-dimethyl-2-phenylethyl)-amino]methyl}-5-pyrimidinemethanol in 10 ml of ethanol, 1.1 g of potassium hydroxide is added. The resulting mixture is heated at 70° C. for 18 hours at which point the reaction mixture is concentrated under reduced pressure. The residue is dissolved in methylene chloride was water. The layers are separated and the aqueous portion further extracted with methylene chloride. The combined organic layers are dried over anhydrous magnesium sulfate and then concentrated to obtain the crude product. Preparative TLC on silica gel yields pure product. Treatment of this product with an ethanolic solution of anhydrous HCl provides the hydrochloride salt of the desired product.

EXAMPLE 11

Preparation of 2-Hydroxy-α-{[(1,1-dimethyl-2-phenylethyl)amino]methyl}-5-pyridinemethanol

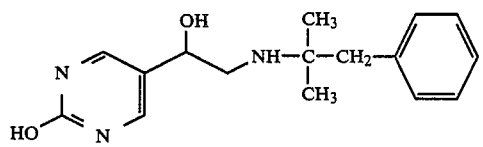

A solution of 100 mg of 2-amino-α-{[(1,1-dimethyl-2-phenylethyl)amino]methyl}-5-pyrimidinemethanol, prepared as described in Example 10, in 5 ml of ethanol is treated with 5 ml of 10N sodium hydroxide solution in a sealed tube. The resulting mixture is heated at 120° C. for 18 hours. The reaction mixture is cooled and then repeatedly extracted with methylene chloride. The combined organic extracts are washed with water and then dried over anhydrous magnesium sulfate. Concentration of this solution resuts a crude product. Preparative TLC on silica gel produces the title compound.

What is claimed is:

1. A compound of the formula

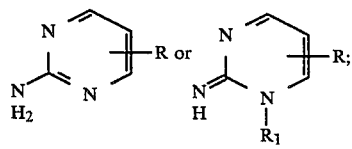

or

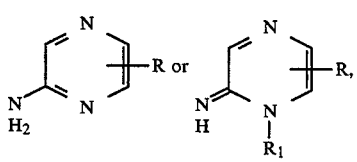

or a pharmaceutically acceptable salt or an enantiomer thereof wherein, $R_1$ is H or OH, R is

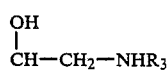

wherein, $R_3$ is

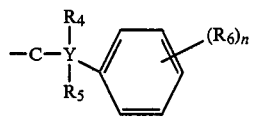

wherein, $R_4$ and $R_5$ are independently selected from H and $C_1$–$C_3$ alkyl, Y is $CH_2$, $(CH_2)_2$, $(CH_2)_3$, $(CH_2)_4$ or —$CH_2$—O—, $R_6$ is H, OH, $OCH_3$, halogen, methylenedioxy or $C_1$–$C_3$ alkyl and n is 1 or 2.

2. A compound of the formula

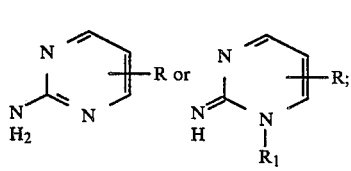

or

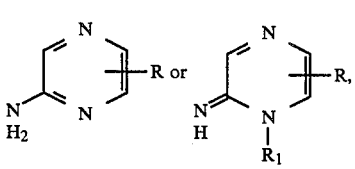

or pharmaceutically acceptable salt or an enantiomer thereof wherein, $R_1$ is H and R is

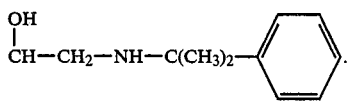

3. A compound of claim 2 having the formula

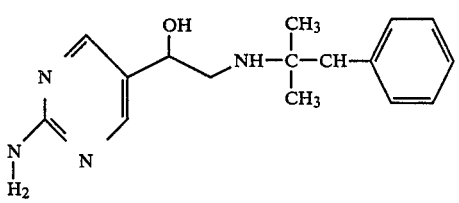

or a tautomer thereof.

4. A pharmaceutical composition for (a) reducing intraocular eye pressure, (b) treating hypertension or (c) effecting bronchodilation containing a compound of claim 1.

5. A method for (a) reducing intraocular eye pressure, (b) treating hypertension or (c) effecting bronchodilation by administering an effective amount of a compound of claim 1 in a suitable dosage form.

6. A method for effecting α- and β-adrenergic blocking activity comprising administering an effective α- and β-adrenergic blocking amount of the compound of claim 1 in a suitable dosage form.

* * * * *

UNITED STATES PATENT AND TRADEMARK OFFICE
CERTIFICATE OF CORRECTION

PATENT NO. : 4,816,457
DATED : March 28, 1989
INVENTOR(S) : John J. Baldwin, Joseph Atkinson & David E. McClure It is certified that error appears in the above-identified patent and that said Letters Patent is hereby corrected as shown below:

In claim 1, col. 36, lines 1-5, delete,

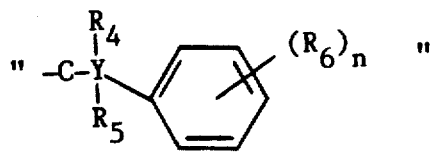

and in its place add,

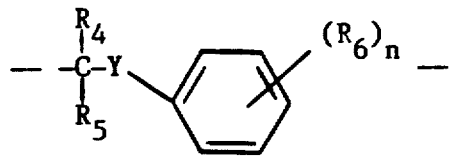

Signed and Sealed this

Tenth Day of July, 1990

*Attest:*

HARRY F. MANBECK, JR.

*Attesting Officer*     Commissioner of Patents and Trademarks